United States Patent
Hall et al.

(10) Patent No.: US 11,883,159 B2
(45) Date of Patent: Jan. 30, 2024

(54) PATIENT RANGE OF MOTION MONITOR

(71) Applicant: DePuy Synthes Products, Inc., Raynham, MA (US)

(72) Inventors: Mark T. Hall, Bridgewater, MA (US); Varun Ramdevan, Newton, MA (US); Michael J. O'Neil, West Barnstable, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 199 days.

(21) Appl. No.: 15/970,619

(22) Filed: May 3, 2018

(65) Prior Publication Data

US 2018/0317813 A1    Nov. 8, 2018

Related U.S. Application Data

(60) Provisional application No. 62/502,019, filed on May 5, 2017.

(51) Int. Cl.
*A61B 5/11* (2006.01)
*G08B 21/18* (2006.01)
(Continued)

(52) U.S. Cl.
CPC .......... *A61B 5/1121* (2013.01); *A61B 5/6892* (2013.01); *A61B 5/7435* (2013.01);
(Continued)

(58) Field of Classification Search
CPC ... A61B 5/1121; A61B 5/6892; A61B 5/7435; A61B 5/7475; A63B 21/4037;
(Continued)

(56) References Cited

U.S. PATENT DOCUMENTS 7,661,309 B2   2/2010  Lan et al.
8,052,629 B2   11/2011 Smith et al.
(Continued)

FOREIGN PATENT DOCUMENTS

WO    2013022890    2/2013

OTHER PUBLICATIONS

Krigslund, R. et al.: "A Novel Technology for Motion Capture Using PAssive UHF RFID Tags", IEEE Transactions on Biomedical Engineering, IEEE Service Center, Piscataway, NJ, USA, vol. 60, No. 5, May 1, 2013, pp. 1453-1457.
(Continued)

*Primary Examiner* — Kerri L McNally
(74) *Attorney, Agent, or Firm* — Barnes & Thornburg LLP (57) ABSTRACT

Technologies for a monitoring system for monitoring a user's movement include a sensor module and a monitoring device. The sensor module is attached to the user or wearable by the user. The monitoring device detects the sensor module positioned in proximity to the monitoring device, receives sensor data from the detected sensor module, analyzes the received sensor data to determine a position and an orientation of the detected sensor module relative to the monitoring device, compares the determined positions of the detected sensor module to predefined planned positions, and initiates an alert notification in response to a determination that a difference between the determined positions of the detected sensor module and the predefined positions is greater than a reference threshold.

19 Claims, 4 Drawing Sheets

(51) Int. Cl.
*A61B 5/00* (2006.01)
*G06F 3/01* (2006.01)
*A63B 24/00* (2006.01)
*A63B 21/00* (2006.01)
*G16H 20/30* (2018.01)

(52) U.S. Cl.
CPC ........ *A61B 5/7475* (2013.01); *A63B 21/4037* (2015.10); *A63B 24/0006* (2013.01); *A63B 24/0062* (2013.01); *A63B 24/0075* (2013.01); *G06F 3/017* (2013.01); *G08B 21/182* (2013.01); *G16H 20/30* (2018.01); *A63B 2024/0015* (2013.01); *A63B 2024/0068* (2013.01)

(58) Field of Classification Search
CPC ............ A63B 24/0006; A63B 24/0062; A63B 24/0075; A63B 2024/0015; A63B 2024/0068; G06F 3/017; G08B 21/182
See application file for complete search history.

(56) References Cited

U.S. PATENT DOCUMENTS

| | | | |
|---|---|---|---|
| 2010/0081895 A1* | 4/2010 | Zand | A61B 5/0002 600/309 |
| 2014/0228649 A1 | 8/2014 | Rayner et al. | |
| 2015/0168002 A1* | 6/2015 | Plitkins | F24F 11/30 165/237 |
| 2017/0164876 A1* | 6/2017 | Hyde | G16H 50/30 |
| 2017/0191695 A1* | 7/2017 | Bruhn | G05B 15/02 |
| 2018/0056184 A1* | 3/2018 | Bentley | A61B 5/6831 |
| 2018/0116560 A1* | 5/2018 | Quinn | A61B 5/1121 |
| 2018/0236308 A1* | 8/2018 | Hyde | A61H 1/00 |
| 2019/0066832 A1* | 2/2019 | Kang | A61B 5/4884 |

OTHER PUBLICATIONS

Occhiuzzi, C. et al.: "The RFID Technology for Neurosciences: Feasibility of Limbs' Monitoring in Sleep Diseases", IEEE Transactions on Information Technology in Biomedicine, IEEE Service Center, Los Alamitos, CA, USA, vol. 13, No. 1, Jan. 1, 2010, pp. 37-43.

Aroca, Rafael V. et al.: "Towards a battery-free wireless smart glove for rehabilitation applications based on RFID", 2015 IEEE Brazil RFID, IEEE, Oct. 7, 2015, pp. 1-5.

Amendola, Sara et al.: "Combined passive radiofrequency identification and machine learning technique to recognize human motion", 2014 44th European Microwave Conference, European Microwave Association, Oct. 6, 2014, pp. 1044-1047.

Lavernia et al., "Accuracy of Knee Range of Motion Assessment after Total Knee Arthroplasty," The Journal of Arthroplasty, 2008, pp. 85-91, vol. 23, No. 6, Suppl. 1, Elsevier Inc.

Pozzi et al., "Physical Exercise after Knee Arthroplasty: A Systematic Review of Controlled Trials," Eur. J. Phys. Rehabilitation Med., Dec. 2013, p. 877-892, vol. 49, No. 6.

Pozyx Laboratories, "Pozyx: accurate real-time indoor positioning," Mar. 15, 2016, 12 pages, Kickstarter.

Sixense, "Stem System: The Best Way to Interact with Virtual Worlds," Oct. 31, 2018, 24 pages, Kickstarter.

* cited by examiner

PATIENT RANGE OF MOTION MONITOR

This application claims priority to U.S. Patent Application Ser. No. 62/502,019, filed May 5, 2017, which is expressly incorporated herein by reference.

TECHNICAL FIELD

The present disclosure relates generally to monitoring systems for monitoring a user's movement, and more particularly to monitoring systems and methods of monitoring a user's range of motion and/or multi-plane joint kinematics for preoperative assessment and post-operative recovery monitoring.

BACKGROUND

Clinicians utilize several means to determine range of motion, including direct observations, goniometers, and flex-extension X-rays. These tools determine ROM and the kinematics of motion in multiple planes both prior to and following surgical intervention. However, the quality of the data from these techniques has been shown to be variable and unreliable, thereby impacting the outcomes of care intervention and operational efficiency. The lack of accurate range of motion and multi-plane joint kinematics data also reduces a care provider's ability to track and compare outcomes from patients, clinicians, and interventions.

SUMMARY

According to one aspect of the disclosure, a monitoring system for monitoring a user's movement includes a sensor module configured to be attached to the user, and a monitoring device having a plurality of anchors. The monitoring device is configured to detect the sensor module positioned in proximity to the monitoring device, receive sensor data from the detected sensor module, analyze the received sensor data to determine a position and an orientation of the detected sensor module relative to the monitoring device, compare the determined positions of the detected sensor module to predefined planned positions, and initiate an alert notification in response to a determination that a difference between the determined positions of the detected sensor module and the predefined positions is greater than a reference threshold.

In some embodiments, the monitoring system may also include a plurality of sensor modules. Each sensor module may be configured to be attached to the user, and the monitoring device may be configured to detect a plurality of sensor modules.

In some embodiments, the monitoring device may be configured to select one or more of detected sensor modules to track movements and orientations of the one or more selected sensor modules based on where the sensor module is attached on the user.

In some embodiments, each of the plurality of anchors may include at least one tag reader configured to detect the sensor module.

In some embodiments, the sensor module may include an inertial measurement unit.

In some embodiments, the sensor module may include one or more biometric sensors.

In some embodiments, one or more anchors may be positioned external to the monitoring device.

In some embodiments, the sensor module may include one or more sensor tags.

In some embodiments, the monitoring device may also include a visual indicator operable to notify the user upon detecting the sensor module.

In some embodiments, the monitoring device may include an audio indicator operable to notify the user upon detecting the sensor module.

In some embodiments, to receive the sensor data from the detected sensor module, the monitoring device may be further configured to receive sensor data from the detected sensor module in response to receiving an input from the user.

In some embodiments, to receive the sensor data from the detected sensor module, the monitoring device may be further configured to receive sensor data upon detecting the sensor module.

In some embodiments, the monitoring device may also include an input device configured to receive an input from the user.

In some embodiments, the input device may be an audio sensor configured to capture voice commands from the user.

In some embodiments, the input device may be a touch screen display configured to receive input from the user.

In some embodiments, the input device may be a graphic user interface that is configured to display one or more physical movement sequences, and receive an input from the user indicative of a physical movement sequence selected from the displayed physical movement sequences.

In some embodiments, the one or more physical movement sequences may be customized based on age, sex, medical history, or physical condition of the user.

In some embodiments, to compare the determined positions of the detected sensor module to predefined planned positions, the monitoring device may be further configured to compare the determined positions of the detected sensor module to predefined positions of the selected physical movement sequence.

In some embodiments, the predefined positions of the selected physical movement sequence may be customized based on age, sex, medical history, or physical condition of the user.

In some embodiments, the monitoring device may be further configured to determine angular velocity of the detected sensor module; and compare the determined angular velocity of the detected sensor module to threshold rates of the selected physical movement sequence.

In some embodiments, the threshold rates of the selected physical movement sequence may be customized based on age, sex, medical history, or physical condition of the user.

In some embodiments, the monitoring device may further include a gesture sensor that is configured to determine movement of the user's body part over the gesture sensor.

In some embodiments, the monitoring device may be a mat sited to permit the user to perform physical movement sequences thereon.

According to another aspect, a method of monitoring a user's movement includes (i) detecting a sensor module positioned in proximity to a monitoring device, (ii) receiving sensor data from the detected sensor module, (iii) analyzing the received sensor data to determine a position and an orientation of the detected sensor module relative to the monitoring device, (iv) comparing the determined positions of the detected sensor module to predefined planned positions, and (v) initiating an alert action in response to a determination that a difference between the determined positions of the detected sensor module and the predefined positions is greater than a reference threshold.

In some embodiments, the method may further include detecting more than one sensor modules attached to the user.

In some embodiments, the method may further include selecting one or more detected sensor modules to track movements and orientations of the selected sensor modules based on where the sensor module is attached on the user.

In some embodiments, the method may further include notifying the user upon detecting the sensor module via a visual indicator.

In some embodiments, the method may further include notifying the user upon detecting the sensor module via an audio indicator.

In some embodiments, receiving the sensor data from the detected sensor module may further include receiving sensor data from the detected sensor module in response to receiving an input from the user.

In some embodiments, the method of receiving the sensor data from the detected sensor module may further include receiving sensor data upon detecting the sensor module.

In some embodiments, the method may further include determining movement of the user's body part over a gesture sensor.

In some embodiments, the method may further include receiving an input from the user via an input device.

In some embodiments, the method of receiving the input from the user via the input device may further include receiving voice commands from the user via an audio sensor.

In some embodiments, the method of receiving the input from the user via the input device may further include receiving an input from the user via a touch screen display.

In some embodiments, the method may further include displaying one or more physical movement sequences on a graphic user interface, and receiving an input from the user indicative of a physical movement sequence selected from the physical movement sequences.

In some embodiments, the one or more physical movement sequences may be customized based on age, sex, medical history, or physical condition of the user.

In some embodiments, the method of comparing the determined positions of the detected sensor module to predefined planned positions may further include comparing the determined positions of the detected sensor module to predefined positions of the selected physical movement sequence.

In some embodiments, the predefined positions of the selected physical movement sequence may be customized based on age, sex, medical history, or physical condition of the user.

In some embodiments, the method may further include determining angular velocity of the detected sensor module, and comparing the determined angular velocity of the detected sensor module to threshold rates of the selected physical movement sequence.

In some embodiments, the threshold rates of the selected physical movement sequence may be customized based on age, sex, medical history, or physical condition of the user.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Terms representing anatomical references, such as anterior, posterior, medial, lateral, superior, inferior, etcetera, may be used throughout this disclosure in reference to a user's natural anatomy. Such terms have well-understood meanings in both the study of anatomy. Use of such anatomical reference terms in the specification and claims is intended to be consistent with their well-understood meanings unless noted otherwise.

Figure 1:
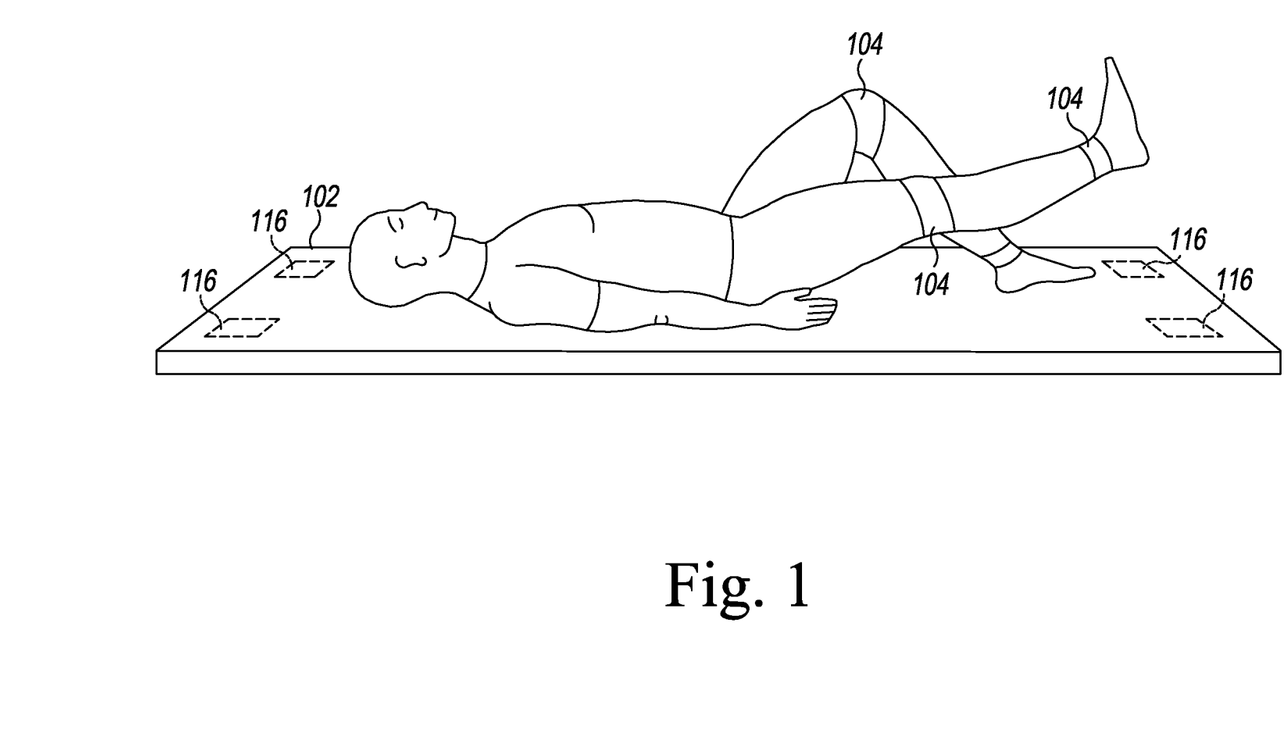
FIG. 1 is a simplified illustration of at least one embodiment of a monitoring platform device and a plurality of sensor modules attached to a user.

Referring to FIG. 1, a monitoring platform device 102 and a plurality of sensor modules 104 attached to a user are shown. In an illustrative embodiment, the sensor modules 104 are embedded in wearable straps that are attached to the user during an exercise (e.g., a range of motion, physiotherapy, yoga, stretching, or any movement performed in vicinity of the monitoring platform device 102). It should be appreciated that, in some embodiments, the sensor modules 104 may be embedded in a garment worn by the user or otherwise secured to the garment. The monitoring platform device 102 is configured to detect one or more sensor modules 104 in vicinity of the monitoring platform device 102 and monitor movements of the detected sensor modules 104 during the exercise by analyzing sensor data received from the each detected sensor module 104, which is described in detail below.

Figure 2:
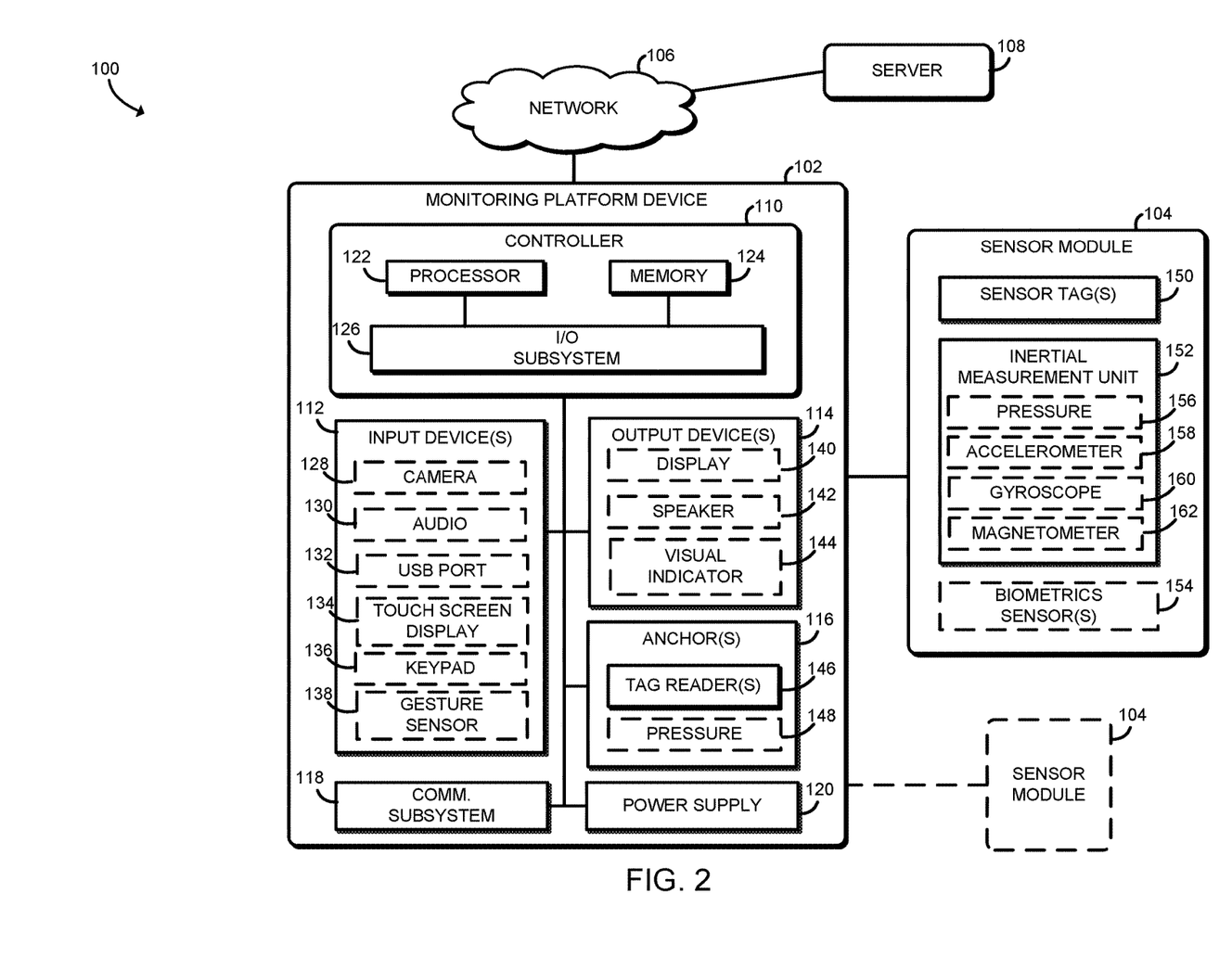
FIG. 2 is a simplified block diagram of at least one embodiment of a monitoring system for monitoring user's range of motion and/or joint kinematics.

Referring now to FIG. 2, a monitoring system 100 for monitoring the user's range of motion and/or joint kinematics is shown. The monitoring system 100 includes the monitoring platform device 102, one or more sensor modules 104, a network 106, and a server 108. In the illustrative embodiment, the monitoring platform device 102 is configured to detect one or more sensor modules 104 and communicate with the detected sensor modules 104 to receive sensor data from one or more sensor tags 150 and an inertial measurement unit 152 of the sensor module 104 to determine a location and an orientation of each sensor module 104.

The monitoring platform device 102 includes a controller 110, one or more input devices 112, one or more output devices 114, one or more anchors 116, a communication subsystem 118, and a power supply 120 that supplies power to the monitoring platform device 102. It should be appreciated that the monitoring platform device 102 may include other or additional components. As shown in FIG. 2, the controller 110 includes a processor 122, a memory 124, and an input/output ("I/O") subsystem 126. In some embodiments, one or more of the illustrative components may be incorporated in, or otherwise form a portion of, another component. For example, the memory 124, or portions thereof, may be incorporated in the processor 122 in some embodiments.

The processor 122 may be embodied as any type of processor capable of performing the functions described herein. For example, the processor 122 may be embodied as a single or multi-core processor(s), digital signal processor, microcontroller, or other processor or processing/controlling circuit. Similarly, the memory 124 may be embodied as any type of volatile or non-volatile memory or data storage capable of performing the functions described herein. In operation, the memory 124 may store various data and software used during operation of the monitoring platform device 102 such as applications, programs, libraries, and drivers. The memory 124 is communicatively coupled to the processor 122 via the I/O subsystem 126, which may be embodied as circuitry and/or components to facilitate input/output operations with the processor 122, the memory 124, and other components of the monitoring platform device 102. For example, the I/O subsystem 126 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 126 may form a portion of a system-on-a-chip (SoC) and be incorporated, along with the processor 122, the memory 124, and other components of the monitoring platform device 102, on a single integrated circuit chip.

The input device 112 may be embodied as any type of device, circuit, or component capable of receiving input from the user of the monitoring platform device 102. The input devices 112 may include a camera 128, an audio sensor 130 (e.g., a microphone), a USB port 132 to be connected to a peripheral device, a graphic user interface or a touch screen display 134, a keypad 136, a gesture sensor 138, or other input devices. For example, in some embodiments, the input devices 112 may include an audio sensor 130 configured to capture voice commands from a user.

Additionally or alternatively, the input devices 112 may include a touch screen display 134 configured to receive input from a user. For example, in some embodiments, the touch screen display 134 may display a list of exercise routines for the user and display the exercise routine selected by the user. The touch screen display 134 may display or demonstrate each movement of the selected exercise routine for a predefined period of time for the user to follow. It should be appreciated that the exercise routine may be physiotherapy treatment regimen. It should also be appreciated that the list of exercise routines may be preprogrammed or preselected by a manufacturer, a healthcare provider, a caregiver, or a user.

In other embodiments, the input devices 112 may include a gesture sensor 138 that is configured to determine a direction of a movement. For example, the gesture sensor 138 may determine whether a user's body part (e.g., a user's limb, hand, or foot), has moved to the left, right, up, down, in (i.e., closer), and out (i.e., further away) relative to the gesture sensor 138. It should be appreciated that the gesture detected by the gesture sensor 138 is used in addition to the sensor data received from the each detected sensor module 104 to detect and analyze the user's movement.

The output device 114 may be embodied as any type of device, circuit, or component capable of generating output to the user of the sensor modules 104 or to the server 108. For example, the output devices 114 may be embodied as, or otherwise include, a display 140, a speaker 142 or other audio output device, one or more visible indicator 144, and/or other output devices. For example, in some embodiments, the output devices 114 may include a display 140 to provide information to the user of the sensor modules 104 during the monitoring process. In such embodiments, the display 140 may be embodied as any type of display capable of displaying digital information such as a liquid crystal display (LCD), a light emitting diode (LED) display, an organic light emitting diode (OLED) display, a plasma display, a cathode ray tube (CRT), or other type of display device. In some embodiments, the monitoring platform device 102 may also include any number of additional input/output devices, interface devices, and/or other peripheral devices. In the illustrative embodiment, the output devices 114 sends a local and/or remote alarm (e.g., display, sound, light, vibrations, or haptic feedback) in response to a determination that the user needs attention based on the user's movement which is discussed in detail below.

The anchor(s) 116 may include, or otherwise be embodied as, any type of sensor, sensor circuit, reader, or other circuit or component capable of sensing, detecting, measuring, or otherwise producing data indicative of the sensor module 104 detected near the monitoring platform device 102. It should be appreciated that the anchor(s) 116 may continuously or periodically detect the sensor module 104 within a local vicinity of the monitoring platform device 102. In the illustrative embodiment, the anchor(s) 116 includes one or more tag readers 146 that are configured to detect the sensor module 104. It should be appreciated that the specific types and number of anchors 116 may depend on the type and number of the sensor module 104. For example, each tag reader 146 of the anchors 116 may be embodied as or otherwise include one or more radio frequency identifier (RFID), ultra-wideband (UWB), and/or near-field communication (NFC) readers that are capable of interrogating and identifying one or more RFID, UWB, and/or NFC tags 150 of the sensor module 104. In some embodiments, the monitoring platform device 102 may include an additional anchor 116 that is embodied as a pressure sensor 148. It should be appreciated that, in some embodiments, the one or more anchors 116 may be positioned external to the monitoring platform device 102. For example, an anchor 116 may be mounted on a various locations in near proximity to the monitoring platform device 102, such as a wall, a floor, and/or furniture.

The communication subsystem 118 may be embodied as any type of communication circuit, device, or collection thereof, capable of enabling communications between the monitoring platform device 102 and the server 108 via the network 106. To do so, the communication subsystem 118 may be configured to use any one or more communication technologies (e.g., wireless or wired communications) and associated protocols (e.g., Ethernet, Bluetooth®, Wi-Fi®, WiMAX, LTE, 4G, 5G, etc.) to effect such communication. In use, as discussed in more detail below, the communication subsystem 118 is configured to transmit sensor data of the sensor module 104 and/or an alert notification to the server 108.

The power supply 120 is configured to control an activation of the monitoring platform device 102. In particular, the power supply 120 supplies power to other components of the monitoring platform device 102 including tag readers 146 of an anchor 116. In the illustrative embodiments, the powered tag readers 146 in turn supplies power to one or more sensor tags 150 of a sensor module 104 via electromagnetic induction.

As described above, the sensor module 104 includes one or more sensor tags 150 and the inertial measurement unit 152. The sensor tag 150 is configured to communicate with the anchor 116 of the monitoring platform device 102. Each sensor tag 150 may be embodied as any data tag, circuitry, device, or physical feature capable of being detected, sensed, or otherwise read by the tag reader(s) 146 of the monitoring platform device 102 and from which the relative location of the sensor tag 150 near the monitoring platform device 102 may be determined. For example, in the illustrative embodiment, each sensor tag 150 is embodied as an RFID, UWB, or NFC sensor tag embedded in or otherwise attached to a wearable strap, and is powered via electromagnetic induction from the tag reader 146. As discussed in more detail below, the sensor tags 150 may transmit tag information, such as a tag identifier that uniquely identifies the corresponding sensor tag 150, to the anchor 116 of the monitoring platform device 102 in response to being sensed or interrogated.

The inertial measurement unit 152 is configured to transmit sensor data that includes an orientation of a sensor module 104. The inertial measurement unit 152 may include a pressure sensor 156, an accelerometer 158, a gyroscope 160, and a magnetometer 162. In some embodiments, the sensor module 104 may further include one or more biometric sensor(s) 154 to transmit the user's biometrics, such as body temperature, heart rate, and perspiration.

The monitoring platform device 102 is configured to communicate with the server 108 via the network 106 to transmit analyzed sensor data of the sensor module 104 and/or alert notifications as discussed in more detail below. In some embodiments, the monitoring platform device 102 may transmit raw sensor data of the sensor module 104 via the network 106 to be processed at the server 108. In the illustrative, the monitoring platform device 102 is configured to communicate with the server 108 via the network 106, for example, a server 108 included in a nurse call system and/or an EMR (electronic medical record) system or a server configured to communicate with a caregiver's mobile or smart device. In some embodiments, the monitoring platform device 102 may communicate via Wi-Fi antenna or other known wireless communication equipment and protocols. Alternatively or additionally, the monitoring platform device 102 may communicate the sensor data to the server 108 via a wired connection.

Figure 3:
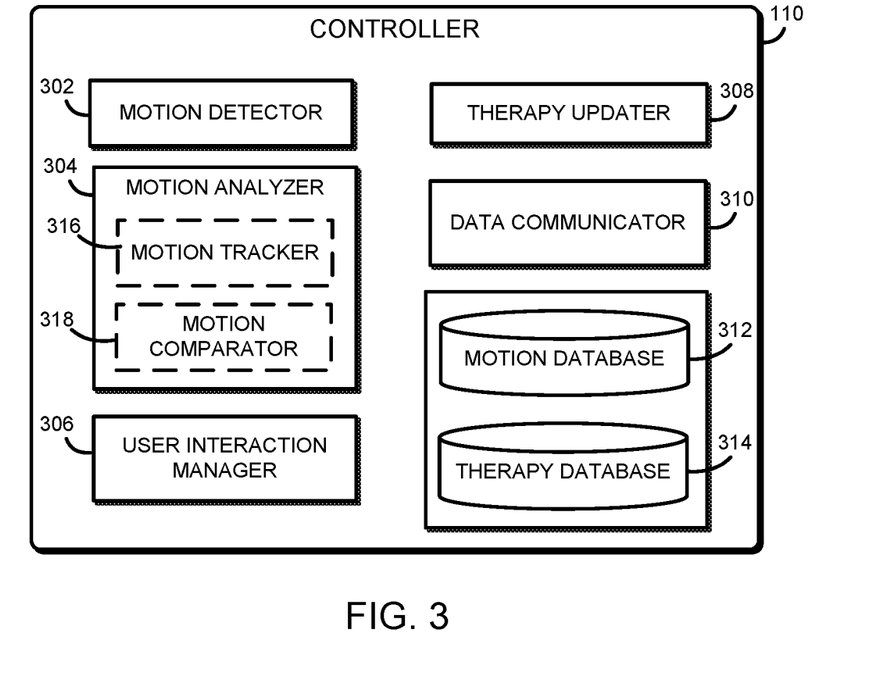
FIG. 3 is a simplified block diagram of at least one embodiment of an environment that may be established by a monitoring platform device of the monitoring system of FIG. 2.

Referring now to FIG. 3, in use, the controller 110 of the monitoring platform device 102 includes a motion detector 302, a motion analyzer 304, a user interaction manager 306, a therapy updater 308, a data communicator 310, a motion database 312, and a therapy database 314.

The motion detector 302 is configured to periodically or continually detect the position and orientation of a detected sensor module 104 relative to each of the corresponding anchors 116 that detected the sensor module 104. For example, the motion detector 302 receives the sensor data from the detected sensor module 104 and determines the position and orientation of the sensor module 104 relative to the monitoring platform device 102 by using trilateration or triangulation based on the received sensor data.

The motion analyzer 304 is configured to analyze the positions and orientations of the detected sensor module 104 relative to the monitoring platform device 102. The motion analyzer 304 includes a motion tracker 316 and a motion comparator 318.

The motion tracker 316 is configured to track positions and orientations of a detected sensor module 104 relative to the monitoring platform device 102 over a period of time. For example, when a user performs an exercise routine stored in the motion database 312 (e.g., range of motion, stretching, or physiotherapy), the motion tracker 316 tracks the consecutive positions and orientations of each detected sensor module 104 during the exercise. In some embodiments, the motion tracker 316 may also determine an angular velocity of each detected sensor module 104 over a predefined time period based on the consecutive positions of the each sensor module 104 during the exercise.

Subsequently, the motion comparator 318 is configured to determine whether received sensor data of a detected sensor module 104 is outside of a reference threshold. For example, in the illustrative embodiment, the motion comparator 318 compares the positions and orientations of the detected sensor module 104 to ideal positions and orientations of the performed exercise stored in the motion database 312. In addition, in some embodiments, the motion comparator 318 may further compare the angular velocity of the detected sensor module 104 to ideal threshold rates of the performed exercise stored in the motion database 312. It should be appreciated that ideal positions, orientations, and threshold rates of exercises may be preprogrammed or preselected by a manufacturer, a healthcare provider, a caregiver, or a user. It should further be appreciated that the ideal positions and threshold rates of exercises may be customized to an individual user depending on age, sex, physical condition(s) (e.g., height, weight), and medical history (e.g., previous orthopaedic surgeries, fractures) of the user.

The user interaction manager 306 is configured to control the communication with a user of the sensor module 104. The user interaction manager 306 controls receiving an input from the user and/or sending an alert to the user. For example, in some embodiments, the user interaction manager 306 controls receiving an input from the user indicative of a start of an exercise via an input device 112 of the platform device 102. In the illustrative embodiment, the user interaction manager 306 also controls sending a local alert to notify the user if the motion analyzer 304 determines that the received sensor data of the detected sensor module 104 is outside of a reference threshold.

The data communicator 310 is configured to control the communication between the monitoring platform device 102 and the sensor modules 104 for receiving sensor data from sensor modules 104. The data communicator 310 is further configured to control the communication between the monitoring platform device 102 and the server 108 for transmitting the received sensor data and/or alert notifications to the server 108 via the network 106.

Figure 4:
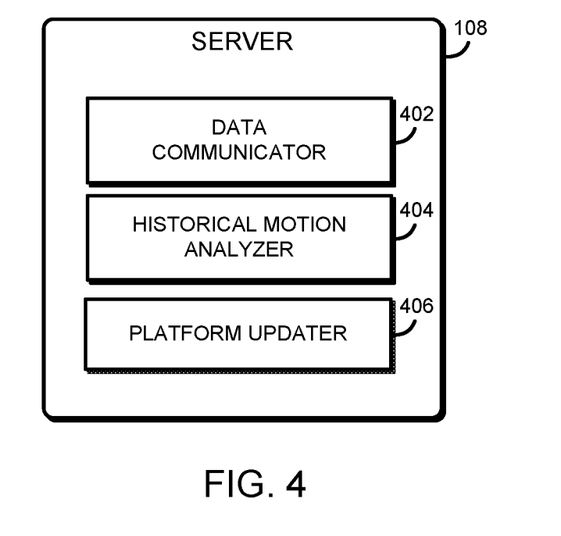
FIG. 4 a simplified block diagram of at least one embodiment of an environment that may be established by a server of the monitoring system of FIG. 2.

Referring to FIG. 4, in use, the server 108 includes a data communicator 402, a historical motion analyzer 404, and a platform updater 406. The data communicator 402 is configured to control the communication between the server 108 and the monitoring platform device 102 for receiving sensor data of one or more sensor modules 104. In the illustrative embodiment, the historical motion analyzer 404 is configured to control analysis of the received sensor data over a predefined period of time. It should be appreciated that the historical motion analyzer 404 is further to monitor the analyzed sensor data to ensure that the user is conforming to recommended exercises and that no adverse events are present.

The platform updater 406 is configured to periodically update monitoring platform data such as an exercise list, positions and orientations during each exercise routine, and threshold rate of movement during each exercise routine. In the illustrative embodiment, the monitoring platform data may be individually customized to the user of the monitoring platform device 102 and the sensor modules 104. For example, the monitoring platform data includes recommended exercises, ideal positions and orientations during each exercise routine, and ideal threshold rates of movements during each exercise routine for the user based on user's age, sex, physical condition(s) (e.g., height, weight), and medical history (e.g., previous orthopaedic surgeries, fractures). The updated monitoring platform data is transmitted to the monitoring platform device 102 via the data communicator 402 for implementation.

Figure 5:
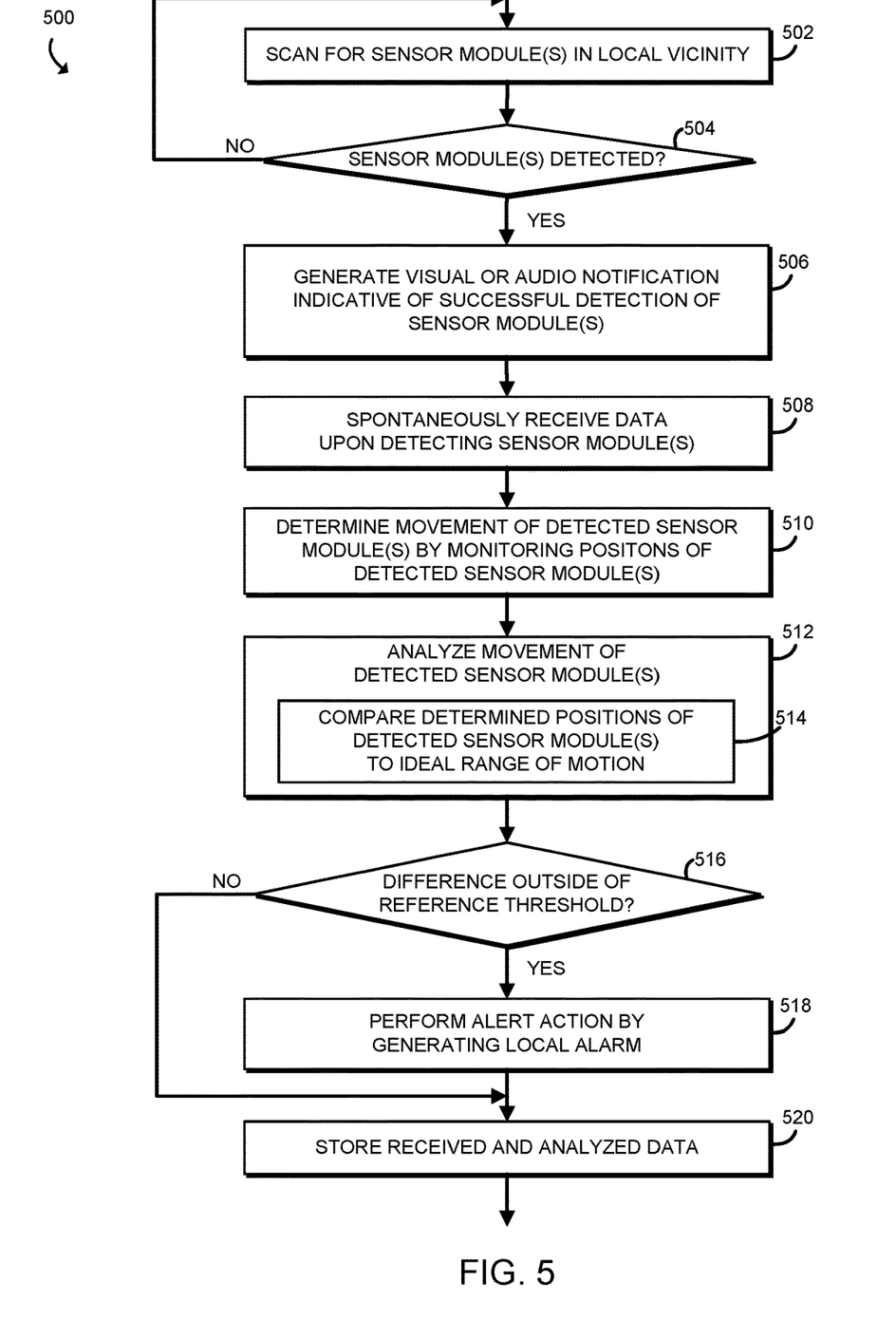
FIG. 5 is a simplified flow diagram of at least one embodiment of a method for monitoring the user's range of motion and/or joint kinematics that may be executed by the monitoring platform device of FIG. 2.

Referring to FIG. 5, in use, the monitoring platform device 102 may execute a method 500 for receiving data from one or more sensor modules 104 that are in vicinity of the monitoring platform device 102. In the illustrative embodiment, the method 500 begins with block 502 in which the monitoring platform device 102 scans for at least one sensor module 104 of a sensor module 104 in the local vicinity of the monitoring platform device 102. To do so, in the illustrative embodiment, the monitoring platform device 102 activates the anchor(s) 116 to generate an electromagnetic field. The anchor(s) 116 than measures the field and seeks for changes in the electromagnetic field or seeks for return signal from one or more sensor modules 104. In some embodiments, the monitoring platform device 102 may generate a visual or audible signal to indicate to the user that the monitoring platform device 102 is searching for a sensor module 104. For example, an LED indicator coupled to the monitoring platform device 102 may be energized to project a colored light or blink while scanning for a sensor module 104.

In block 504, the monitoring platform device 102 determines whether a sensor module 104 has been detected. If not, the method 500 loops back to block 502 to continue to scan for another sensor module 104. If, however, the monitoring platform device 102 determines that a sensor module 104 has been detected in the local vicinity of the monitoring platform device 102, the method 500 advances to block 506.

In block 506, the monitoring platform device 102 generates a visual or audio notification to indicate that at least one sensor module 104 has been detected and the monitoring platform device 102 is ready to receive data from the detected sensor module(s) 104. For example, an LED light may change color or from a blinking light to a non-blinking light. In the illustrative embodiment, the monitoring platform device 102 continues and generate an electromagnetic field periodically to measure a magnetic field reading.

In the illustrative embodiment, the monitoring platform device 102 is configured to receive sensor data of each detected sensor module 104 upon the detection of the sensor module(s) 104 in block 508. For example, the sensor module 104 may transmit inertial measurements of the sensor module 104, such as pressure sensor readings, accelerometer readings, gyroscope readings, and magnetometer readings. In some embodiments, the sensor module 104 may further transmit biometric sensor readings (e.g., heart rate, temperature). It should be appreciated that the monitoring platform device 102 may be configured to ignore sensor data from sensor module 104 that are not in proximity with the monitoring platform device 102.

When the monitoring platform device 102 receives the sensor data from the detected sensor module(s) 104, the method 500 proceeds to block 510. In block 510, the monitoring platform device 102 determines movement of the detected sensor module(s) 104 by monitoring the positions and orientations of the detected sensor module(s) 104 relative to the monitoring platform device 102. To do so, the monitoring platform device 102 periodically determines the position and orientation of each detected sensor module 104 relative to the monitoring platform device 102 at a given time. In the illustrative embodiment, the monitoring platform device 102 determines the position of the detected sensor module 104 based on periodical magnetic field readings of one or more sensor tags 150 of the detected sensor module 104. The monitoring platform device 102 further determines the orientation of the sensor module 104 based on the corresponding sensor data received from an inertial measurement unit 152 of the sensor module 104 at the time of each magnetic field reading. The monitoring platform device 102 continually determines positions and orientations of each detected sensor module 104 in order to monitor the change in positions and orientations of each sensor module 104. In some embodiments, the monitoring platform device 102 may also determine an angular velocity of each detected sensor module 104 over a predefined time period based on the consecutive positions of each of the sensor modules 104. It should be appreciated that, in some embodiments, all the received sensor data may be transmitted to the server 108 to be processed and analyzed by the server 108.

Subsequently, in block 512, the monitoring platform device 102 further analyzes the movement of each of the detected sensor module(s) 104. To do so, in some embodiments, in block 514, the monitoring platform device 102 may compare the plurality of determined positions and orientations of each detected sensor module 104 to predefined positions and orientations of an ideal range of motion over a predefined time period to determine whether the difference is outside of a predefined threshold. In some embodiments, the monitoring platform device 102 may further compare the determined angular velocity of each detected sensor module 104 to a predefined threshold rate of the ideal range of motion. As discussed above, positions, orientations, and threshold rate of an ideal range of motion may be preprogrammed or preselected by a manufacturer, a healthcare provider, a caregiver, or a user. It should further be appreciated that the predefined ideal range of motion may be customized to an individual user depending on age, sex, physical condition(s) (e.g., height, weight), and medical history (e.g., previous orthopaedic surgeries, fractures) of the user.

In block 516, the method 500 determines whether the difference determined in block 514 is outside of a corresponding reference threshold. If not, the method 500 advances to block 520 to store the received sensor data from the detected sensor module(s) 104 and the analyzed sensor data of the received sensor data. It should be appreciated that, in some embodiments, the monitoring platform device 102 may also transmit the received sensor data and the analyzed sensor data to the server 108. If, however, the different is outside of the reference threshold, the method 500 advances to block 518.

In block 518, the monitoring platform device 102 performs an alert action. To do so, the monitoring platform device 102 generates a local alarm. The local alarm may be, for example, a visual notification via a LED indicator coupled to the monitoring platform device 102 or an audio notification via a speaker coupled to the monitoring platform device 102. It should be appreciated that, in some embodiments, visual or audio indicators may be coupled to the sensor module 104. In such embodiments, the monitoring platform device 102 may transmit an alert notification to a sensor module 104. In other embodiments, the monitoring platform device 102 may transmit an alert notification to the server 108. In addition, the monitoring platform device 102 may transmit the received and analyzed sensor data to the server 108 in addition to the alert notification. In yet other embodiments, the monitoring platform device 102 may transmit an alert notification to a smart device of a caregiver or a doctor that has been wirelessly connected to the monitoring platform device 102. It should be appreciated that, in some embodiments, a smart device may be connected to the monitoring platform device 102 via a wire. For example, if the monitoring platform device 102 is located at a healthcare facility, the monitoring platform device 102 may be coupled to a system (e.g., a nurse system) via wired connection. Subsequently, the method 500 proceeds to block 520 in which the monitoring platform device 102 stores the received sensor data from the detected sensor module(s) 104 and the analyzed sensor data of the received sensor data.

Many further embodiments of the present application are envisioned. For example, it should be appreciated that, in some embodiments, to receive sensor data from the detected sensor tag(s) 150 in block 508, the monitoring platform device 102 may receive sensor data upon receiving a start input signal from a user. For example, a user may press a hard button or a touch screen coupled to the monitoring platform device 102 and/or the sensor tag 150 to indicate that the user wants to monitor the user's movement. In other embodiments, the user may select a physiotherapy regimen on a touch screen or a user's smart device coupled to the monitoring platform device 102. In such embodiments, the monitoring platform device 102 receives the sensor data when a physiotherapy regimen is selected by the user. It should be appreciated that the monitoring platform device 102 may be configured to ignore the sensor data from sensor tags 150 that are not in proximity with the monitoring platform device 102.

When monitoring the detected sensor tag(s) 150 based on the received sensor data in block 510, in some embodiments, the monitoring platform device 102 may determine pressure that has been applied on each detected sensor tag 150. In other embodiments, the monitoring platform device 102 may ignore sensor data received from a disinterested sensor tag(s) 150. For example, as discussed above, the monitoring platform device 102 receives the sensor data when a user may select a desired physiotherapy regimen on a touchscreen coupled to the monitoring platform device 102. If the user has a multiple sensor tags 150 attached to the user, the monitoring platform device 102 may determine which sensor tags 150 are associated with the selected physiotherapy regimen, and may ignore other sensor tag(s) 150 that are not associated with the selected physiotherapy regimen. It should be appreciated that, in some embodiments, all the received sensor data may be transmitted to the server 108 to be processed and analyzed by the server 108.

When analyzing the movement of each of the detected sensor tag(s) 150 in block 512, in some embodiments, the monitoring platform device 102 may compare the determined positions of each of the detected sensor tags 150 to positions of a selected physiotherapy regimen. For example, as discussed above, the monitoring platform device 102 receives sensor data when a user may select a desired physiotherapy regimen on a touchscreen coupled to the monitoring platform device 102. Each physiotherapy regimen includes routine positions. The monitoring platform device 102 compares the determined positions of each detected sensor tag 150 to the positions of a selected physiotherapy regimen over a predefined time period to determine whether the difference is outside of a predefined threshold. In some embodiments, the monitoring platform device 102 may further compare the determined angular velocity of each detected sensor tag 150 to a predefined threshold rate of each action of the selected physiotherapy regimen.

In some embodiments, some of the procedures discussed above as being executed by the monitoring platform device 102 may be instead performed by the server 104.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A monitoring system for monitoring a user's movement, comprising:
   a sensor module configured to be attached to the user, and
   a monitoring platform device comprising:
   a plurality of anchors configured to detect the sensor module positioned in proximity to the monitoring platform device, and
   a controller including a motion detector and a motion analyzer,
   wherein the motion detector is configured to receive sensor data from the detected sensor module,
   wherein the motion analyzer is configured to analyze the received sensor data to determine a position and an orientation of the detected sensor module relative to the monitoring platform device indicative of a sensed range of motion of the user and to compare the determined positions of the detected sensor module to predefined planned positions associated with an ideal range of motion of the user, and wherein the controller is configured to initiate an alert notification in response to the motion analyzer determining that a difference between the determined positions of the detected sensor module and the predefined positions is greater than a reference threshold indicating that the sensed range of motion of the user is outside of the ideal range of motion of the user.

2. The monitoring system of claim 1 further comprising:
a plurality of sensor modules, each sensor module being configured to be attached to the user,
wherein the plurality of anchors of the monitoring platform device are configured to detect the plurality of sensor modules.

3. The monitoring system of claim 1, wherein each of the plurality of anchors includes at least one tag reader configured to detect the sensor module.

4. The monitoring system of claim 1, wherein to receive the sensor data from the detected sensor module comprises to receive sensor data from the detected sensor module in response to receiving an input from the user.

5. The monitoring system of claim 1, wherein to receive the sensor data from the detected sensor module comprises to receive sensor data upon detecting the sensor module.

6. The monitoring system of claim 1, wherein the monitoring platform device further includes an input device configured to receive an input from the user.

7. The monitoring system of claim 6, wherein the input device is a graphic user interface that is configured to:
display one or more physical movement sequences, and
receive an input from the user indicative of a physical movement sequence selected from the displayed physical movement sequences.

8. The monitoring system of claim 7, wherein the one or more physical movement sequences are customized based on age, sex, medical history, or physical condition of the user.

9. The monitoring system of claim 7, wherein to compare the determined positions of the detected sensor module to predefined planned positions comprises to compare the determined positions of the detected sensor module to predefined positions of the selected physical movement sequence.

10. The monitoring system of claim 7, wherein the motion analyzer is further configured to:
determine angular velocity of the detected sensor module; and
compare the determined angular velocity of the detected sensor module to threshold rates of the selected physical movement sequence.

11. The monitoring system of claim 1, wherein the monitoring platform device further includes a gesture sensor that is configured to determine movement of the user's body part over the gesture sensor.

12. The monitoring system of claim 1, wherein the monitoring platform device is a mat sized to permit the user to perform physical movement sequences thereon.

13. A method of monitoring a user's movement, comprising:
detecting a sensor module positioned in proximity to a monitoring platform device,
receiving sensor data from the detected sensor module with the monitoring platform device,
analyzing the received sensor data with the monitoring platform device to determine a position and an orientation of the detected sensor module relative to the monitoring platform device indicative of a sensed range of motion of the user,
comparing, with the monitoring platform device, the determined positions of the detected sensor module to predefined planned positions associated with an ideal range of motion of the user, and
initiating an alert action with the monitoring platform device in response to a determination that a difference between the determined positions of the detected sensor module and the predefined positions is greater than a reference threshold indicating that the sensed range of motion of the user is outside of the ideal range of motion of the user.

14. The method of claim 13 further comprising:
detecting more than one sensor modules attached to the user, and
selecting one or more detected sensor modules to track movements and orientations of the selected sensor modules based on where the sensor module is attached on the user.

15. The method of claim 13, wherein receiving the sensor data from the detected sensor module comprises receiving sensor data from the detected sensor module in response to receiving an input from the user.

16. The method of claim 13 further comprising:
displaying one or more physical movement sequences on a graphic user interface, and
receiving an input from the user indicative of a physical movement sequence selected from the physical movement sequences.

17. The method of claim 16, wherein the one or more physical movement sequences are customized based on age, sex, medical history, or physical condition of the user.

18. The method of claim 16, wherein comparing the determined positions of the detected sensor module to predefined planned positions comprises comparing the determined positions of the detected sensor module to predefined positions of the selected physical movement sequence.

19. The method of claim 16 further comprising:
determining angular velocity of the detected sensor module, and
comparing the determined angular velocity of the detected sensor module to threshold rates of the selected physical movement sequence.

* * * * *